(12) United States Patent
Simpson et al.

(10) Patent No.: US 6,676,606 B2
(45) Date of Patent: Jan. 13, 2004

(54) ULTRASONIC DIAGNOSTIC MICRO-VASCULAR IMAGING

(75) Inventors: David Hope Simpson, Kenmore, WA (US); Jeffry E. Powers, Bainbridge Island, WA (US); Michael Schauf, Bothell, WA (US); Cyrille Villet, Kirkland, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/170,178

(22) Filed: Jun. 11, 2002

(65) Prior Publication Data

US 2003/0229285 A1 Dec. 11, 2003

(51) Int. Cl.$^7$ ................................................. A61B 8/14
(52) U.S. Cl. ..................................................... 600/458
(58) Field of Search .............................. 600/407, 430, 600/431, 437, 438, 440–458; 367/7, 11, 130, 138; 73/625, 626; 128/916; 601/2, 3; 424/9.51, 9.52

(56) References Cited

U.S. PATENT DOCUMENTS

| | | |
|---|---|---|
| 4,888,694 A | 12/1989 | Chesarek |
| 5,706,819 A | 1/1998 | Hwang et al. |
| 5,833,613 A | 11/1998 | Averkiou et al. |
| 5,879,303 A | 3/1999 | Averkiou et al. |
| 6,036,643 A | 3/2000 | Criton et al. |
| 6,095,980 A | 8/2000 | Burns et al. |
| 6,171,246 B1 | 1/2001 | Averkiou et al. |
| 6,186,950 B1 | 2/2001 | Averkiou et al. |
| 6,193,662 B1 | 2/2001 | Hwang |
| 6,352,511 B1 * | 3/2002 | Hossack et al. ............. 600/443 |
| 6,436,049 B1 * | 8/2002 | Kamiyama et al. ......... 600/458 |
| 6,461,303 B2 * | 10/2002 | Angelsen ..................... 600/458 |
| 6,464,643 B1 * | 10/2002 | Brock-Fisher .............. 600/458 |
| 6,517,489 B1 * | 2/2003 | Phillips et al. .............. 600/458 |
| 6,533,728 B1 * | 3/2003 | Belohlavek et al. ........ 600/458 |

* cited by examiner

*Primary Examiner*—Ali M. Imam
(74) *Attorney, Agent, or Firm*—W. Brinton Yorks, Jr.

(57) ABSTRACT

A method and apparatus are described for ultrasonically imaging tiny blood vessels with the aid of a contrast agent. The locations of microbubbles of the contrast agent are detected in a series of images as the microbubbles move through the blood vessels. These images are temporally processed to identify the moving microbubbles, and persistence processed to depict images which show the tracks followed by the microbubbles through the blood vessels. A maximum intensity persistence can be used to show the steady buildup of microbubble tracks through the vasculature, or a slow decay employed so that the tracks will fade to black over time.

21 Claims, 3 Drawing Sheets

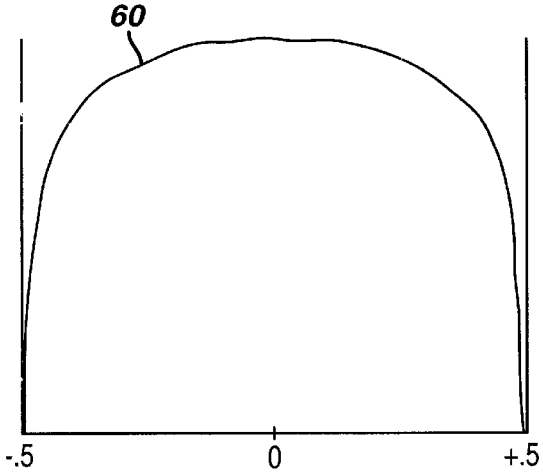
FIG. 6a
FIG. 5
Line of Sight
|      | 1  | 2  |
|------|----|----|
| PRI  |    |    |
| 1    | \|+ |    |
| 2    | \|- |    |
| 3    |    | \|+ |
| 4    |    | \|- |
| 5    | \|+ |    |
| 6    | \|- |    |
| 7    |    | \|+ |
| 8    |    | \|- |
| 9    | \|+ |    |
| 10   | \|- |    |
| 11   |    | \|+ |
| 12   |    | \|- |
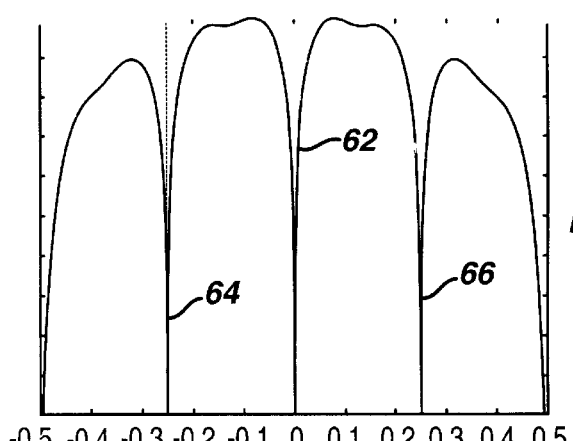
FIG. 6b
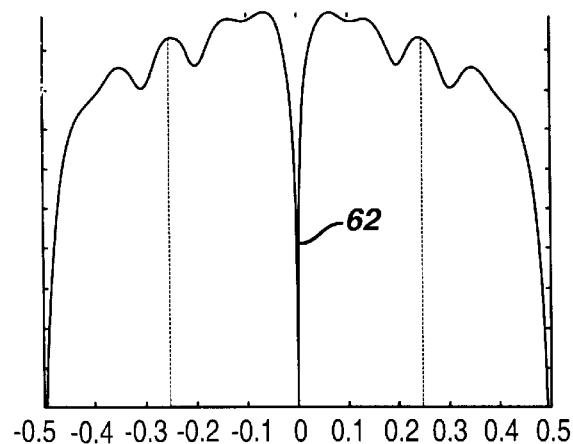
FIG. 6c

ULTRASONIC DIAGNOSTIC MICRO-VASCULAR IMAGING

This invention relates to ultrasonic diagnostic imaging systems and, in particular, to ultrasonic diagnostic imaging systems for imaging micro-vascular systems with contrast agents.

Ultrasonic contrast agents enable clinicians to image and quantify structures and functions in the body which are not otherwise readily seen or measured. The ability of ultrasonic contrast agents to resonate nonlinearly when excited with ultrasound can produce a strong harmonic response, enabling clear segmentation of vessels infused with the contrast agent. A sharply defined image can be produced by disrupting the microbubbles of the contrast agent with high MI ultrasound as described in U.S. Pat. No. 5,456,257. The ability to follow the progress of a contrast agent as it infuses the blood vessels of tissue makes it possible to produce measures of myocardial perfusion using contrast, as described in U.S. Pat. No. 5,833,613.

Recent studies of lesions such as breast lesions have focused on the vasculature of the lesion. Early detection of breast lesions and definition of the lesion boundaries can often be ascertained by using ultrasound to look for characteristic vascular structures. In addition, changes in lesion growth and development such as those resulting from chemotherapy often manifest themselves at an early point in time by changes in the lesion vasculature. It is anticipated that these studies may be aided by the use of contrast agents. However, the vascular structures involved are tiny, micro-vascular structures with individual vessels conducting minute amounts of blood flow at very low rates of flow. It would be desirable to be able to use contrast enhanced ultrasound to image and delineate such difficult to detect micro-vascular structures.

In accordance with the principles of the present invention, ultrasound is used to image micro-vascular structures with the aid of a contrast agent. The harmonic response of the contrast agent reduces clutter, and temporal persistence is used to discern the structure of the micro-vasculature by delineating the track of microbubbles through the tiny vessels.

In the drawings:

FIG. 5 illustrates compound interleave pulse inversion sequences in accordance with a further aspect of the present invention; and FIGS. 6a–6c illustrate Doppler filter characteristics which may be obtained through compound interleave pulse inversion in accordance with the present invention.

In contrast-enhanced ultrasonic imaging with microbubble contrast agents, conditions sometimes exist in which the effective concentration of microbubbles in tissue or blood is sufficiently low that individual microbubbles or clusters of microbubbles moving through a vessel appear as point targets in corresponding ultrasound images. The punctate appearance of the contrast agent in these images can make it difficult to identify the architecture of blood vessels in the images. Improving the visibility of such blood vessels is of clinical significance, since the morphology of blood vessels may be used for the detection and, in some cases, differentiation of suspicious lesions. The following apparatus and method improve the visibility of blood vessels and blood flow patterns by using temporal frame to frame processing of ultrasound contrast images.

Figure 1:
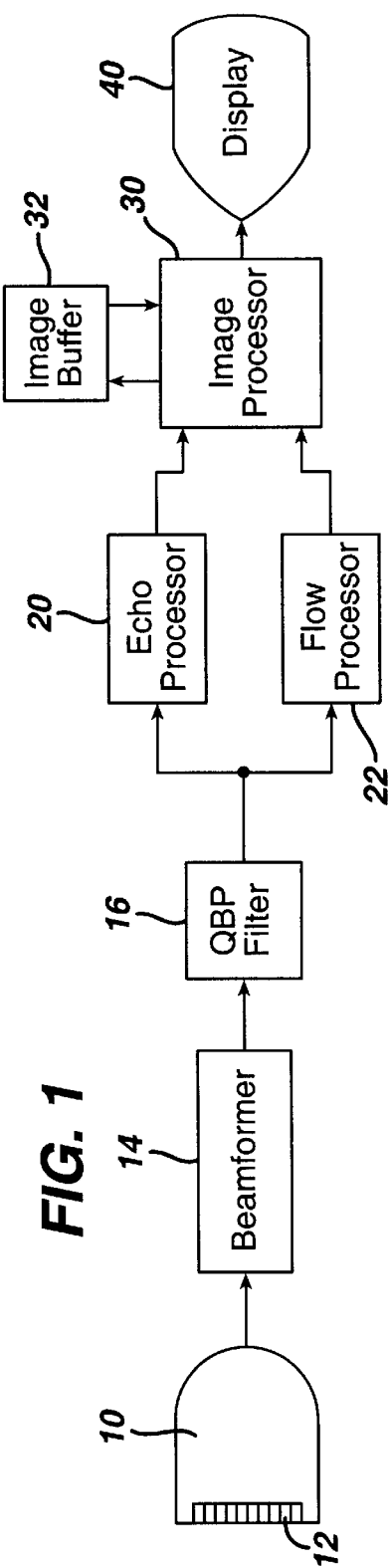
FIG. 1 illustrates in block diagram form an ultrasonic diagnostic imaging system constructed in accordance with the principles of the present invention.

Referring to FIG. 1, an ultrasonic diagnostic imaging system constructed in accordance with the principles of the present invention is shown in block diagram form. A probe 10 includes an array transducer 12 which transmits ultrasound beams into a subject and receives echoes from along the beam directions in response to the transmit beams, all under control of a beamformer 14. Echo signals produced by the beamformer are demodulated into quadrature I,Q components by a quadrature bandpass (QBP) filter 16. Quadrature bandpass filters are well known in the art such as those described in U.S. Pat. No. 6,454,714, entitled "Ultrasonic Harmonic Flash Suppression." The echo samples are coupled to an echo processor 20 where the samples are processed for B mode display by amplitude detection and log compression. The echo samples are also coupled to a flow processor 22 where they are used for Doppler estimation as described in U.S. Pat. Nos. 5,386,830, 6,036,643, and 6,095,980. The processed echo and flow signals are coupled to an image processor 30 where they are scan converted into the desired image format and displayed on a display 40 either separately or combined. A sequence of two dimensional images may be stored in an image buffer 32 where they may be replayed for more detailed study, or processed as by rendering to form a three dimensional image or image sequence.

Figure 2:
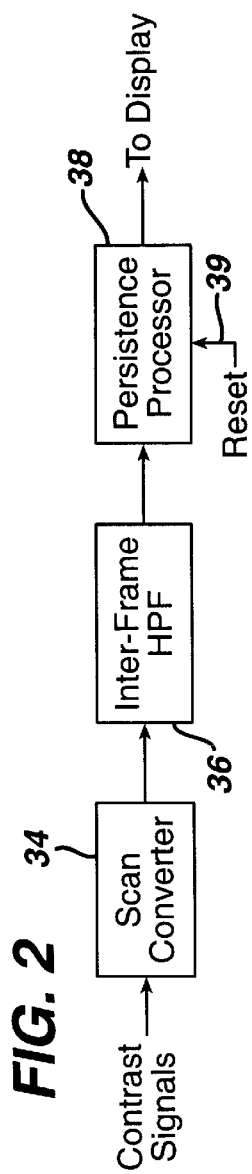
FIG. 2 illustrates details of the image processor of FIG. 1.

In accordance with the principles of the present invention the image processor performs frame-to-frame image processing for contrast-enhanced ultrasound imaging. A first embodiment of an image processor of the present invention is shown in FIG. 2. The image processor includes a scan converter 34 which converts received contrast signals into a desired display format, such as a rectangular or sector-shaped image. The scan converted images are then filtered by an inter-frame high pass filter 36. The inter-frame high pass filter 36 is a temporal filter that may take the form of an FIR filter, an IIR filter or a frame-to-frame differentiator which filters successive images on a pixel-by-pixel basis. Spatially corresponding pixels which are the same from frame to frame, such as pixels of stationary tissue, will produce a low- or zero-level output. Pixels which differ from frame to frame, as will occur when a microbubble moves into a pixel location or out of a pixel location from frame to frame, will produce a finite output level for display. The inter-frame high pass filter 36 thus reduces signals from stationary and quasi-stationary objects such as tissue and produces display level signals from moving microbubbles in the vasculature.

The high pass filtered contrast agent signals are applied to a persistence processor 38 which sustains a temporal sequence of detected microbubbles in the image. The persistence processor can have a time constant for the persistence of a displayed microbubble which is greater than zero and as great as one. As the individual microbubble detection events build up (persist) in the image over time, the morphology of the tiny blood vessels through which they are passing becomes visible. The persistence processor 38 can be operated with a high time constant, showing the continual passage of microbubbles through blood vessels and a continual buildup of the flow structure on the screen. The persistence processor can also be given a lower time constant so that microbubble events will slowly decay away with time. Preferably the user is given a reset control 39 to reset the persistence to black at the start of an acquisition sequence or after a high time constant sequence has filled the screen with microbubble events or after tissue or transducer motion. It may further be desirable to combine the transmission of a high MI transmit frame with the reset control 39, causing the reset of the persistence processor to coincide with a high energy frame which strongly disrupts the microbubbles currently in the image region.

A preferred persistence processor operates in accordance with:

$$\text{OutputPixel}(x,y,k) = \max\{\text{abs}[\text{InputPixel}(x,y,k)], P*\text{OutputPixel}(x,y,k-1)\}$$

where the time constant P has a range of $0 < P \leq 1$. When the time constant P is less than one, the trail of displayed microbubble events will exhibit a fast attack, slow decay brightness that will start as a bright event, then fade to black over time. When the time constant P is equal to one, the persistence processor will perform a maximum intensity projection of the current (k) and previous (k−1) pixel brightnesses.

While the apparatus and method of the present invention can be used when detecting contrast agents in the fundamental mode, it is preferable to carry out the inventive technique in the harmonic mode, to take advantage of the strong segmentation and clutter rejection benefits of harmonic contrast operation. While a radiofrequency high pass filter can be used to pass the harmonic echo components in preference to the fundamental components, a preferred way to separate the harmonic echo components of the contrast signal is by pulse inversion as described in U.S. Pat. No. 5,706,819. As is well known, the pulse inversion technique involves the transmission of two or more transmit events of differently modulated (phase or polarity or amplitude or a combination thereof) transmit pulses along the same beam direction. Echoes received in response to the two transmit events are combined on a spatial basis. Opposite (inverse) phase or amplitude modulation of the transmit pulses will cause fundamental signals of the two events to cancel, while nonlinear (harmonic) components will reinforce each other and thus be separated from the fundamental. The term "pulse" as used in pulse inversion generally refers to the complete transmit-receive cycle of each differently modulated transmit pulse. Thus, two-pulse pulse inversion refers to the transmission of two differently modulated pulses, the reception of echo sequences following each transmit pulse or wave, and the combining of the two echo sequence on a spatial (depth) basis. Pulse inversion of more than two pulses may be employed with the present invention as described in U.S. Pat. No. 6,186,950. Pulse inversion may also be performed by transmitting differently modulated pulses in adjacent beam directions, then separating the harmonic components by interpolation between beam locations as described in U.S. Pat. No. 6,193,662.

In the embodiment of FIGS. 1 and 2, pulse inversion harmonic separation is performed prior to scan conversion by the scan converter 34. A convenient implementation is to use a line buffer following the beamformer 14 in which the echo sequence from one pulse is stored while a second, differently modulated echo sequence is acquired. The two sequences are combined to attenuate the fundamental components and accentuate the harmonic components of the contrast echo signals. The harmonic contrast echoes are filtered by the QBP filter 16 and processed by the echo processor 20. The echo data is scan converted and the image frames are temporally high pass filtered and persistence processed for display as described above.

The ability of a constructed embodiment of the present invention to depict blood vessel morphology is illustrated by the exemplary image sequence of FIGS. 4a–4f. These depict images of a real time image sequence that may develop over the time period of one to three heart cycles, for instance. In an early image in the sequence shown in FIG. 4a, some clutter is seen in the near field in the 0–1 cm range, and five microbubbles are seen in the 1–3 cm range. The five microbubbles are depicted because they appeared in different locations in consecutive frames, causing frame-to-frame subtraction (temporal high pass filtering) to produce finite display signals from the moving microbubbles. Signals from stationary tissues in consecutive frames, either fundamental (linear) or harmonic (nonlinear), will appear in the same location from frame to frame, and will be suppressed by the temporal high pass filter. Thus, clutter due to fundamental signal scattering will be reduced by the use of harmonic signals, and stationary tissue clutter will be diminished by the temporal high pass filter, thereby enabling the moving microbubbles to be distinguished in the image.

Figure 4C:
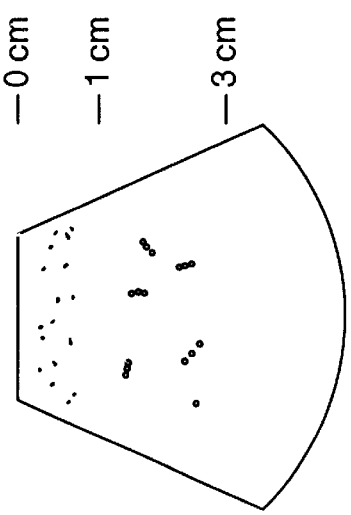
FIGS. 4a–4f illustrate the display of microbubbles flowing through micro-vascular structures in accordance with the principles of the present invention.
Figure 4F:
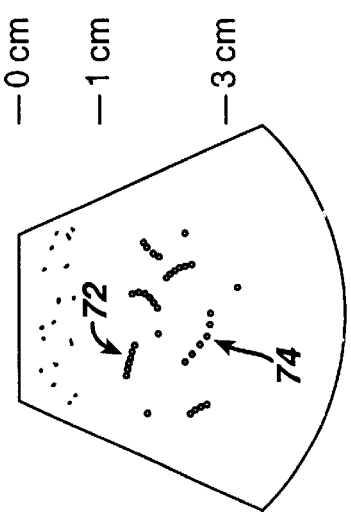
Figure 4B:
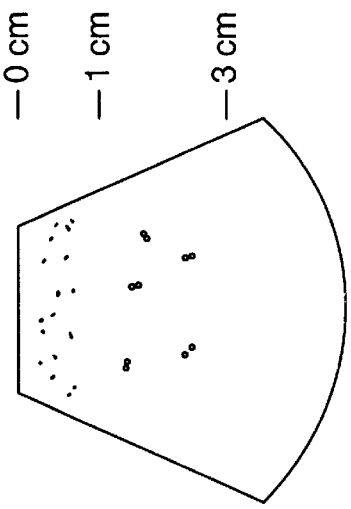
Figure 4E:
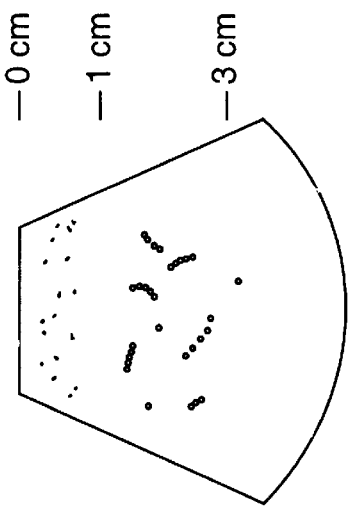
Figure 4A:
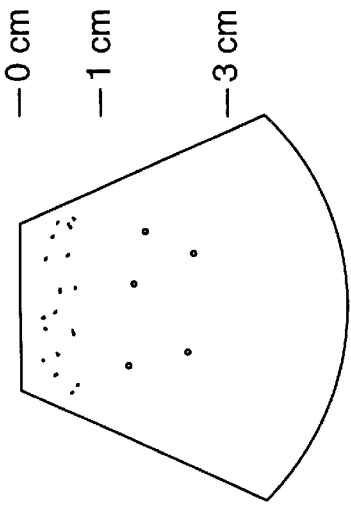
Figure 4D:
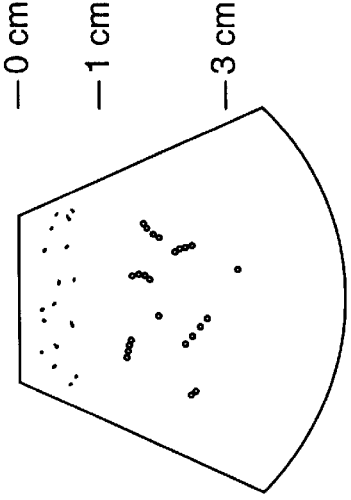

At a later time the image of FIG. 4b is produced. This image shows the five microbubble events which were earlier seen in FIG. 4a due to persistence processing. This image also shows the five microbubbles at new, adjacent locations as the microbubbles move through the micro-vessels in which they are flowing. At a later time the image of FIG. 4c is produced. This image shows the previous locations of the five microbubbles by reason of persistence, and updated locations of the five microbubbles identified by temporal filtering. In this image, and in the later images of FIGS. 4d, 4e, and 4f, the tracks produced by the persisted, successive microbubble locations are seen to delineate the tortuous paths of the small blood vessels in which they are flowing. In addition, other tracks begin to appear as the contrast agent begins to reach other blood vessels in the image plane and begins to define their flow paths. FIG. 4f would inform the clinician that six small vessels are located in the 1–3 cm range of the imaged sector, which may lead to the diagnosis of the presence of a lesion. It is possible that the track of six successive microbubble positions, as seen at 72 and 74 in FIG. 4f, could be caused by six adjacent vessels which are orthogonal to the image plane, but this is unlikely with longer tracks. The clinician can test this hypothesis by moving the probe slightly and reacquiring the microbubbles to test for a vessel in the image plane.

If a time constant of P=1 is used, the sequence of images will contain an ever-increasing buildup of microbubble tracks until the region of the tracks is virtually all white, The persistence processor can then be reset by the clinician and another sequence acquired. Alternatively, a lower value of P<1 can be used, and the older spots in the microbubble track will fade away with time, enabling the image region to be observed for a considerable period of time before needing to be reset.

It is desirable to conduct microbubble tracking as described above at relatively low transmit power levels (low MI) so that the microbubbles will not be destroyed by the ultrasonic energy but will survive over a period of many frames and be detected as they move through the microvasculature. However, it has been found that the procedure is effective even when there is some disruption of the microbubbles in the vessels by the transmit energy, as usually a sufficient presence of microbubbles will survive over a period of several heart cycles.

Figure 3:
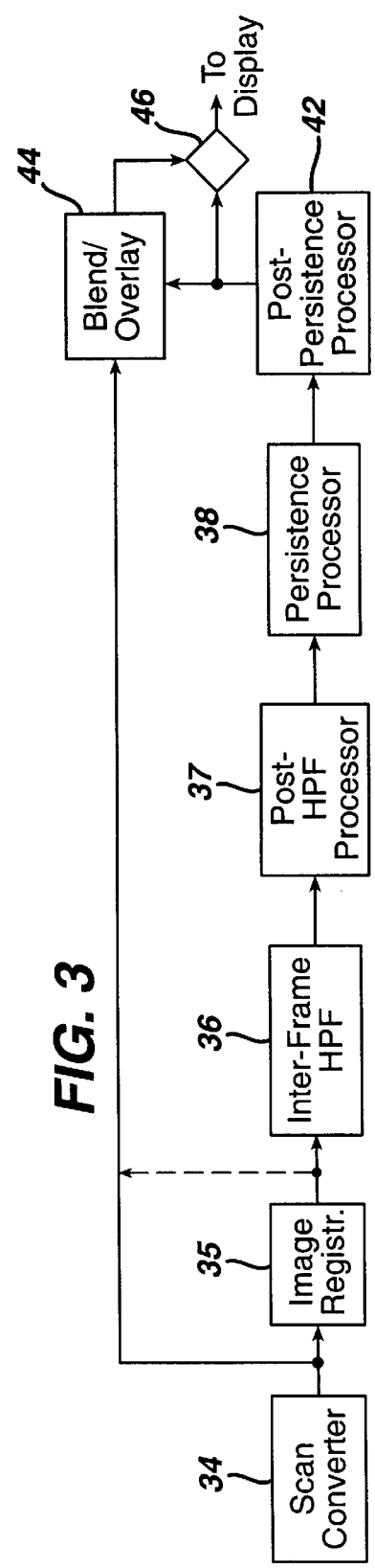
FIG. 3 illustrates a preferred embodiment of an image processor of an ultrasound system constructed in accordance with the principles of the present invention.

A preferred image processor is shown in block diagram form in FIG. 3. Because the embodiment of FIG. 2 uses a temporal high pass filter, it will be sensitive to some degree to probe motion. One way to reduce unwanted effects from probe motion is by harmonic flash suppression, as described in the aforementioned U.S. Pat. No. 6,454,714. Another approach, which may be used separately or in conjunction with flash suppression, is to perform image registration 35 prior to the inter-frame high pass filter 36, as shown in FIG. 3. Gross image registration from frame to frame can reduce the blurring of tissue/transducer motion and will lead to a more effective temporal filter. The post-HPF processor 37 can perform image processing tasks such as thresholding, noise reduction, or frame-to-frame speckle tracking. The post-persistence processor 42 may perform image processing such as edge enhancement or segmentation/thresholding. The processed contrast image may be blended with a conventional 2D echo image. The contrast image may also be segmented and applied as a color overlay over the 2D echo image as indicated by the blend/overlay processor 44. Either may be done with or without image registration, but if the contrast image is registered, it is desirable that the 2D image be registered also so that probe and tissue motion are equally diminished in both images.

The tracks of microbubbles produced by an embodiment of the present invention can be used to calculate the absolute velocity of blood flow through the micro-vasculature. The bubbles can be seen to move a finite amount between frames along the curved paths of the micro-vasculature. Since the scale of the pixel density relative to the anatomy being displayed is known, the distance traveled by a microbubble over a period of frames can be measured in an image. From the knowledge of the frame rate (in frames per second) and the distance a microbubble has moved, the absolute velocity of the flow through the micro-vasculature can be calculated.

Other temporal display techniques may also be used. The flow into a lesion often shows a clearly pulsatile characteristic as it builds up in the lesion, eventually filling the lesion. Arteries will be filled early in the filling period, with the capillary bed being filled in the latter part of the filling period. Vessels appearing in the early stage of filling can be color coded differently than those filled in the latter stage, giving a visual distinction between arteries and the capillary bed.

In accordance with a further aspect of the present invention, slowly flowing contrast agents are detected by a compound interleave of pulse inversion pulse ensembles, providing clutter rejection with improved sensitivity to very low velocity blood flow at high acquisition frame rates. In conventional pulse inversion Doppler imaging, it is desirable to have a Doppler frequency filter with a wide stop band at the Nyquist frequency to attenuate tissue signals, which requires a high sampling frequency (PRF, or pulse repetition frequency) and a narrow stop band at DC to sharply attenuate signals from entirely stationary objects, which requires a long sampling time between the first and last PRI's (pulse repetition intervals). If a total of M pulses per line of sight (beam direction) are required, then NxM pulses must be transmitted, producing an effective Doppler sample frequency of PRF/N, a total dwell time per line of Nx(M1)/PRF, and a frame interval proportional to NxM.

In accordance with the principles of the present invention, compound interleaving of pulse inversion pulse sequences is used to produce filters with the desired characteristics in relatively short sampling times. This provides a highly sensitive imaging technique for detecting low flow rates using pulse inversion Doppler operating at high acquisition frame rates. One such pulse sequence is shown in FIG. 5 for two lines of sight or beam directions. The numbers at the left are a numbered sequence of the pulse repetition intervals (PRIs) used. During the first two PRIs two differently modulated pulses are transmitted in the first line of sight. The different modulation, which could be amplitude, phase, or polarity, is indicated by the "+" and "−" signs adjacent to each PRI line. The echoes of these two pulses are spatially combined to separate the harmonic components. Preferably these two pulses are transmitted in rapid succession so as to reduce motional artifacts in the received echoes, which can result in incomplete fundamental component cancellation.

Another two pulse sequence is transmitted in the second line of sight during PRIs 3 and 4. These pulses are also differently modulated so that the harmonics of the received echoes can be separated by pulse inversion combining of the received echoes. If a third line of sight were used, the next two pulse transmission would be in the third line. After all of the lines of sight of the sequence have been interrogated by a pair of pulses, the transmitter returns to the first line of sight. In the illustration in which the sequence only uses two lines of sight, pulses are transmitted along the first line of sight in PRIs 5 and 6. As the drawing indicates, both lines of sight are interrogated by rapid, two-pulse sequences in this time-interleaved manner until the full ensemble length has been completed, which in the illustration is three pulse-pairs in length. Each line of sight in this example is sampled by a plurality of fast PRF, two-pulse ensembles which together comprise a slow PRF ensemble length of three.

The resulting samples are used in a Doppler filter such as a matrix wall filter. Separate filters can be used for the fast PRF and slow PRF filters, or the two can be combined in a single filter. Suitable separate filter coefficients are:

$$\text{Fast time filter} = [.5 \ .5], \quad \text{Slow time filter} = \begin{matrix} 2 & -1 & -1 \\ -1 & 2 & -1 \\ -1 & -1 & 2 \end{matrix}$$

The first filter has a frequency response which attenuates fundamental tissue signals at the Nyquist limits of the sampling rate as shown by the Doppler filter response characteristic 60 in FIG. 6a. The slow time filter will provide a sharp attenuation to this characteristic at DC as shown by the Doppler filter response 62 in FIG. 6b, which attenuates nonlinear signals from stationary microbubbles and tissue harmonics. Slow moving contrast, which will have a Doppler frequency in the vicinity of zero, will be passed on either side of this central null.

The frequency response characteristic for this example also is seen to exhibit two other intermediate nulls about halfway between DC and the Nyquist limits of ±0.25 PRF. These nulls are not likely to affect the result obtained from very slow rates of flow, but can come into play and cause signal drop-out during high flow conditions. In accordance with a further aspect of the present invention, these intermediate nulls are diminished by using aperiodic time-interleaved sequences. The slow time ensemble is made aperiodic by varying the timing of one or more of the fast time ensembles. Another approach to aperiodic compounding is to vary the interleave ratio over consecutive image frames. An example of an aperiodic compound interleave sequence is:

| Line number | Temporal sequence of pulses |
|---|---|
| 1 | [1, 1, 0, 0, 0, 0, 1, 1, 0, 0, 1, 1, 0, 0] |
| 2 | [0, 0, 1, 1, 0, 0, 0, 0, 1, 1, 0, 0, 1, 1] | where each "1" in the sequence indicates that a modulated pulse of some sort is transmitted and echoes received during the particular pulse repetition interval. In this example it is seen that a fast time sequence of two pulses is transmitted and received along line 1, followed by transmission and reception of a fast time sequence of two pulses along line 2. During the next two pulse intervals no pulses are transmitted along either line. Thereafter fast time sequences of two pulses are alternately transmitted along the two lines. The aperiodicity of the slow time ensembles caused by skipping transmission of the normally recurring second fast time ensemble in PRIs 5 and 6 (for line 1) and PRIs 7 and 8 (for line 2) causes the frequency response of the filter to be rippled without sharp intermediate nulls, as shown in FIG. 6c, a result which is also aided by expected spectral broadening.

The aperiodic interleaving of fast time sequences can be extended to conventional Doppler operating in the fundamental mode with or without contrast agents. Aperiodic interleave and sampling make it possible to generate a Doppler wall filter using very few samples that mimics the performance of wall filters generated with much longer ensemble lengths. For example, consider the following interleave of four pulses over three lines:

| Line number | Temporal sequence of pulses |
|---|---|
| 1 | [1, 0, 0, 0, 0, 1, 0, 0, 1, 0, 0, 0, 0, 1, 0, 0] |
| 2 | [0, 1, 0, 0, 0, 0, 1, 0, 0, 1, 0, 0, 0, 0, 1, 0] |
| 3 | [0, 0, 1, 0, 0, 0, 0, 1, 0, 0, 1, 0, 0, 0, 0, 1] |

A wall filter using samples from this aperiodic ensemble will have low frequency performance similar to an ensemble length of 14, (the PRI duration from the first to the last sample along each line) but with only four samples per filter. Preferably the velocity estimation algorithm used will be modified in consideration of the aperiodicity of the sampling.

The use of aperiodic slow time ensembles may find particular utility in real time three dimensional imaging. In real time 3D it is desirable to be able to scan the entire volumetric region in as short a time as possible, to obtain a high frame rate of display. For Doppler imaging in 3D, a high aliasing cutoff frequency and long (in time) slow time ensembles are desirable in order to detect both high and low flow rates. Traditionally these demands are satisfied by transmitting a long sequence of high PRF pulses down each line, causing long acquisition times and slow frame rates. A time interleaved, aperiodic scan such as that shown above will interrogate each line over a long period of time from the first pulse interval to the last pulse interval, thereby providing good low flow rate sensitivity. The aperiodic timing between consecutive acquisitions along each line provides a high effective aliasing (Nyquist) frequency. Since only a few pulses are needed for each line, many lines can be time interleaved at the cost of only a reduction in the signal to noise ratio of the resultant Doppler estimates.

Embodiments of the present invention can operate on either demodulated echo samples or r.f. data. The fast time ensembles can be more than two pulses in length, such as the three, four, and five pulse ensembles for pulse inversion described in the aforementioned U.S. Pat. No. 6,186,950.

What is claimed is:

1. A method for ultrasonically imaging with an ultrasonic contrast agent comprising:
    transmitting pulses to an image region of a subject;
    receiving echoes from a contrast agent in the image region in response to the transmitted pulses;
    detecting the location of a contrast agent in the image region at a given point in time; and
    producing an image showing the locations of the contrast agent at different points in time.
2. The method of claim 1, further comprising:
    forming an image in response to the received echoes; and
    wherein detecting comprises temporally high pass filtering temporally different images to detect the location of a contrast agent at a given point in time.
3. The method of claim 2, wherein temporally high pass filtering comprises performing frame-to-frame subtraction on a spatial basis of temporally different image frames.
4. The method of claim 3, wherein temporally high pass filtering comprises performing frame-to-frame subtraction on a spatial basis of successive image frames.
5. The method of claim 1, wherein producing an image comprises producing an image in which the display of the location of a contrast agent at a given point in time persists over a plurality of image intervals.
6. The method of claim 5, wherein producing an image comprises displaying a maximum intensity projection of the locations of a contrast agent.
7. The method of claim 5, wherein producing an image comprises displaying the location of a contrast agent at a given point in time with a slow decay persistence over a plurality of image intervals.
8. The method of claim 5, wherein producing an image comprises processing image pixel data on a spatial basis in accordance with:

$$\text{OutputPixel}(x,y,k) = \max\{\text{abs}[\text{InputPixel}(x,y,k)], P*\text{OutputPixel}(x,y,k-1)\},$$

where x and y are pixel coordinates, P is a time constant ranging from 0 to 1, and k is a time marker.

9. A method for ultrasonically imaging with an ultrasonic contrast agent comprising:
    producing a first data set of the location of a moving contrast agent at a first time;
    producing a second data set of the location of the moving contrast agent at a second time; and
    producing an image for display which depicts the locations of the moving contrast agent at the first and second times.
10. The method of claim 9, further comprising temporally high pass filtering the first and second data sets.
11. The method of claim 10, wherein temporally high pass filtering the first and second data sets comprises performing subtraction of the first and second data sets on a spatial basis.
12. The method of claim 9, wherein producing an image for display comprises persistence processing contrast agent location information.
13. The method of claim 9, wherein the contrast agent is a harmonic contrast agent and wherein producing an image for display comprises producing an image showing the path of movement of a contrast agent over time.
14. A method for ultrasonically imaging with an ultrasonic contrast agent comprising:

producing a first data set of the location of a moving harmonic contrast agent at a first time;

producing a second data set of the location of the moving harmonic contrast agent at a second time; and producing an image for display which depicts a track of the locations of the moving harmonic contrast agent at different points in time.

15. An ultrasonic imaging system for harmonic contrast imaging comprising:

an array transducer which interrogates an image field containing a moving contrast agent;

a receiver coupled to the array transducer which produces coherent echo signals from the moving contrast agent;

an image processor coupled to the receiver which produces images showing the locations of the moving contrast agent at different points in time;

an inter-frame high pass filter coupled to the image processor;

a persistence processor coupled to the inter-frame high pass filter which produces images depicting the locations of the moving contrast agent at earlier points in time; and an image display.

16. The ultrasonic imaging system of claim 15, wherein the inter-frame high pass filter comprises a frame-to-frame subtractor.

17. The ultrasonic imaging system of claim 15, wherein the persistence processor utilizes a persistence time constant to cause the location of the moving contrast agent at a given point in time to persist over a plurality of image intervals.

18. The ultrasonic imaging system of claim 17, wherein the persistence time constant causes the location of the moving contrast agent at a given point in time to persist indefinitely.

19. The ultrasonic imaging system of claim 17, wherein the persistence time constant causes the location of the moving contrast agent at a given point in time to persist with a slow decay.

20. The ultrasonic imaging system of claim 15, wherein the image display acts to display an image depicting the tracks of microbubbles through small blood vessels over time.

21. The ultrasonic imaging system of claim 15, further comprising an image registration processor coupled to the image processor.

* * * * *